US009693833B2

(12) United States Patent
Mottola et al.

(10) Patent No.: US 9,693,833 B2
(45) Date of Patent: Jul. 4, 2017

(54) ABSORBENT CLEANING AND SECUREMENT DEVICES AND METHODS

(71) Applicant: Merit Medical Systems, Inc., South Jordan, UT (US)

(72) Inventors: Jim Mottola, Salt Lake City, UT (US); Franklin J. Miller, Poway, CA (US); Philippe Reb, Themericourt (FR)

(73) Assignee: Merit Medical Systems, Inc., South Jordan, UT (US)

( * ) Notice: Subject to any disclaimer, the term of this patent is extended or adjusted under 35 U.S.C. 154(b) by 368 days.

(21) Appl. No.: 14/450,788

(22) Filed: Aug. 4, 2014

(65) Prior Publication Data
US 2015/0034122 A1 Feb. 5, 2015

Related U.S. Application Data

(60) Provisional application No. 61/862,172, filed on Aug. 5, 2013.

(51) Int. Cl.
*A61B 90/70* (2016.01)
*A61B 90/80* (2016.01)
(Continued)

(52) U.S. Cl.
CPC .............. *A61B 90/70* (2016.02); *A61B 90/80* (2016.02); *A47L 13/16* (2013.01); *A47L 13/17* (2013.01);
(Continued)

(58) Field of Classification Search
CPC ... A61B 90/70; A61B 2090/701; A61B 19/34; A61B 2019/343; A61B 90/80;
(Continued)

(56) References Cited

U.S. PATENT DOCUMENTS 4,098,728 A    7/1978  Rosenblatt
4,164,054 A *  8/1979  Hanson ................ G01F 23/045
                                                  15/220.4
(Continued)

FOREIGN PATENT DOCUMENTS

EP    0189375    7/1986
EP    0745104    3/1998
(Continued)

OTHER PUBLICATIONS

Abdeen, et al., "Enhancement of Crude Oil Biodegradation by Immobilizing of Different Bactreial Strains on Porous PVA Hydrogels or Combining of them with their Produced Biosurfactants", Petroleum & Environmental Biotechnology, vol. 5, Issue 5, 2014, 1-10.
(Continued)

*Primary Examiner* — Mark Spisich
(74) *Attorney, Agent, or Firm* — Stoel Rives LLP

(57) ABSTRACT

An absorbent cleaning device for use during a surgical procedure is disclosed. The absorbent cleaning device may comprise a substantially non-fibrous or non-particulate absorbent material and at least one opening. The opening may comprise a slit or channel and be configured to accommodate a portion of a medical appliance or an elongate medical device. The absorbent cleaning device may be configured to clean the medical appliance or the elongate medical device. The absorbent cleaning device may also be configured to retain or secure a medical appliance or elongate medical device during a surgical procedure.

18 Claims, 8 Drawing Sheets

(51) Int. Cl.

| | | |
|---|---|---|
| A47L 13/17 | (2006.01) | |
| A47L 13/16 | (2006.01) | |
| B08B 1/00 | (2006.01) | |
| A61C 19/00 | (2006.01) | |
| A61M 25/00 | (2006.01) | |
| A61M 25/02 | (2006.01) | |

(52) U.S. Cl.
CPC ....... *A61B 2090/701* (2016.02); *A61C 19/002* (2013.01); *A61M 25/02* (2013.01); *A61M 2025/0019* (2013.01); *B08B 1/001* (2013.01)

(58) Field of Classification Search
CPC ......... A61B 19/36; A61C 19/002; B08B 1/00; B08B 1/001; B08B 1/003; B08B 1/006; A47L 13/16; A47L 13/17; A47L 21/00; A47L 21/04
USPC ............ 15/104.04, 218, 218.1, 220.4, 244.4; D32/35, 40, 43
See application file for complete search history.

(56) References Cited

U.S. PATENT DOCUMENTS

| | | | | |
|---|---|---|---|---|
| 4,506,404 | A * | 3/1985 | Clay ...................... | A61B 90/70 15/218.1 |
| 4,517,702 | A * | 5/1985 | Jackson ................. | A61B 1/122 15/114 |
| 4,663,358 | A | 5/1987 | Hyon et al. | |
| 4,866,806 | A * | 9/1989 | Bedford ................. | A61B 90/80 15/104.94 |
| 5,016,401 | A * | 5/1991 | Mangus ................. | A61B 18/14 15/218.1 |
| 5,231,728 | A * | 8/1993 | Schillinger ........... | G01F 23/045 15/220.4 |
| 5,274,874 | A * | 1/1994 | Cercone ................ | A61B 1/122 15/118 |
| 5,477,581 | A * | 12/1995 | Wind ...................... | B08B 1/00 15/210.1 |
| 5,789,464 | A | 8/1998 | Muller | |
| 7,260,863 | B2 * | 8/2007 | Kaufman ................ | A46B 7/04 15/114 |
| 7,763,006 | B2 * | 7/2010 | Tennican ............ | A61M 39/165 604/187 |
| 2007/0033753 | A1 * | 2/2007 | Kritzler ................. | A61B 1/122 15/104.93 |
| 2008/0010766 | A1 * | 1/2008 | Kaufman ................ | A46B 7/04 15/114 |
| 2009/0126134 | A1 * | 5/2009 | Whipple ................. | A61C 3/00 15/104.94 |

FOREIGN PATENT DOCUMENTS

| | | | |
|---|---|---|---|
| JP | 2000-60877 | * | 2/2000 |
| WO | 2004017495 | | 8/2004 |

OTHER PUBLICATIONS

Bansal, "Water-Based Polymeric Nanostructures for Agricultural Applications", Dissertation, 2010, 182 pgs.
Bodugoz, et al., "Preparation of Poly (Vinyl Alcohol) Hydrogels with Radiation Grafted Citric and Succinic Acid Groups", Radiation Physics and Chemistry, 55, 1999, 667-671.
Buist, et al., "The Mechanism of Oxidation of a-Glycols by Periodic Acid. Part X. The Oxidation of Pinacol, and a General Discussion of the Stability of Periodate Esters and their Role in the Mechanism of Oxidation", J. Chem. Soc. (B), 1971, 2128-2142.
Cavalieri, et al., "Study of Gelling Behavior of Poly(Vinyl Alcohol)-Methacrylate for Potential Utilizations in Tissue Replacement and Drug Delivery", Biomacromolecules, 5, 2004, 2439-2446.
Chaouat, et al., "A Novel Cross-Linked Poly (Vinyl Alcohol) (PVA) for Vascular Grafts", Advanced Functional Materials, 18, 2008, 2855-2861.
Chung, et al., "Surface Engineered and Drug Releasing Pre-Fabricated Scaffolds for Tissue Engineering", Advanced Drug Delivery Reviews, 59, 2007, 249-262.
Crispim, et al., "Addition of Methacryloil Groups to Poly (Vinyl Alcohol) in DMSO Catalyzed by TEMED: OptimizationThrough Response Surface Methodology", Elsevier, Polymer Testing, 25, 2006, 377-383.
Crispim, et al., "Hydrogels Based on Chemically Modified Poly (Vinyl Alcohol) (PVA-GMA) and PVA-GMA/Chondroitin Sulfate: Preparation and Characterization", eXPRESS Polymer Letters, vol. 6, No. 5, 2012, 383-395.
Dutta, "Synthesis and Characterization of y-Irradiated PVA/PEG/CaC12 Hydrogel for Wound Dressing", American Journal of Chemistry, 2(2), 2012, 6-11.
El-Mohdy, et al., "Biodegradability, Antimicrobial Activity and Properties of PVA/PVP Hydrogels Prepared by y-Irradiation", J. Polym Res, 16, 2009, 1-10.
Gohil, et al., "Studies on the Cross-Linking of Poly (Vinyl Alcohol)", Journal of Polymer Research, 13, 2006, 161-169.
Gupta, et al., "Interpenetrating Network Superporous Hydrogels for Gastroretentive Application—Preparation, Swelling and Mechanical Properties", Turk J Pharm Sci, 9(2), 2012, 127-138.
Hassan, et al., "Structure and Applications of Poly (Vinly Alcohol) Hydrogels Produced by Conventional Crosslinking or by Freezing/Thawing Methods", Advances in Polymer Science, vol. 153, 2000, 38-65.
Laurent, "D'un Materiau Innovant vers un Pansement Actif et un Substitut Cutane", HAL Archives—Ouvertes, Universite de Cergy Pontoise, 2012.
Lewis, et al., "Polymeric and Self Assembled Hydrogels: Biomedica Applications of Hydrogels: Poly(Vinyl Alcohol)-Based Hydrogels for Embolotherapy and Drug Delivery", Monographs in Supramolecular Chemistry, Edited by Xian Jun Loh and Oren A. Scherman, Chapter 10, 2013, 232-252.
Lima, et al., "Thermal Crosslilnking in Membranes of Polyvinyl Alcohol for use as Cartilage", 21st Brazilian Congress of Mechanical Engineering, Oct. 2011.
Martens, et al., "Characterization of Hydrogels Formed From Acrylate Modified Poly(Vinyl Alcohol) Macromers", Elsevier, Polymer, 41, 2000, 7715-7722.
Martens, et al., "Synthesis and Characterization of Degradable Hydrogels Formed From Acrylate Modified Poly(Vinyl Alcohol) Macromers", Elsevier, Polymer, 43, 2002, 6093-6100.
Mishra, et al., "Radiation Induces crosslilnking Effect on Semi-Interpenetrating Polymer Networks fo Poly(Vinyl Alcohol)", eXPRESS Polymer Letters, vol. 1, No. 7, 2007, 407-415.
Muscatello, et al., "Poly (Vinyl Alcohol) Rehydratable Photonic Crystal Sensor Materials", Advanced Functional Materials, 18, 2008, 1186-1193.
Nuttleman, et al., "Synthesis and Characterization of Photocrosslinkable, Degradable Poly (Vinyl Alcohol)-Based Tissue Engineering Scaffolds", Biomaterials, 23, 2002, 3617-3626.
Parvin, et al., "Preparation and Characterization of Gamma Irradiated Sugar Containing Starch/Poly (Vinly Alcohol)-Based Blend Films", J Polym Environ, 19:, 2011, 1013-1022.
Parvin, et al., "Preparation and Characterization of Starch/PVA Blend for Biodegradable Packaging Material", Advanced Material Research, vols. 123-125, 2010, 351-354.
Patachia, et al., "Tailoring of Poly(Vinyl Alcohol) Cryogels Properties by Salts Addition", eXPRESS Polymer Letters, vol. 3, No. 5, 2009, 320-331.
Peppas, et al., "Ultrapure Poly(Vinyl Alcohol) Hydrogels with Mucoadhesive Drug Delivery Characteristics", European Journal of Pharmaceutics and Biopharmaceutics, 43, 1997, 51-58.
Philipp, et al., "Three Methods for In Situ Cross-Linking of Polyvinyl alcohol Films for Application as Ion-conducting Membranes in Potassium Hydroxide Electrolyte", NASA Technical Paper 1407, Apr. 1979.

(56) References Cited

OTHER PUBLICATIONS

Rafat, et al., "Dual Functionalized PVA Hydrogels that Adhere Endothelial Cells Syngeristically", Biomaterials, 33, 2012, 3880-3886.

Razzak, et al., "Irradiation of Polyvinyl Alcohol for Polyvinyl Pyrrolidone Blended Hydrogel for Wound Dressing", Radiation Physics and Chemistry, 62, 2001, 107-113.

Razzak, et al., "The Characterization of Dressing Component Materials and Radiation Formation of PVA-PVP Hydrogel", Radiation Physics and Chemistry, 55, 1999, 153-165.

Riyajan, et al., "Effect of Potassium on the Physical Property of PVA", Proceedings of the 7th IMT-GT UNINET and the 3rd International PSU-UNS Conferences on Bioscience, 2010, 220-223.

Rojas, et al., "Functionalization and Crosslinking of Microcrystalline Cellulose in Aqueous Media: A Safe and Ecomonic Approach", International Journal of Pharmaceutical Sciences Review and Research, vol. 8, Issue 1, 2011, 28-36.

Schmedlen, et al., "Photocrosslinkable Polyvinyl Alcohol Hodrogels that can be Modified with Cell Adhesion Peptides for use in Tissue Engineering", Biomaterials, 23, 2002, 4325-4332.

Sharaf, et al., "Mechanical and Relaxation Properties of y-Irradiated PVA doped with Ferrous Sulphate", Polymer Degradation and Stability, 66, 1999, 173-177.

Sirousazar, et al., "Dehydration Kinetics of Polyvinly Alcohol Hydrogel Wound Dressing During Wound Healing Process", Chinese Journal of Polymer Science, vol. 28, No. 4, 2010, 573-580.

Stauffer, et al., "Poly(Vinyl Alcohol) Hydrogels Prepared by Freezing-Thawing Cyclic", Polymer, vol. 33, No. 18, 1992, 3932-3936.

Xiao, et al., "Synthesis and Properties of Starch-G-Poly (Maleic Anhydride-Co-Vinly Acetate)", eXPRESS Polymer Letters, vol. 4, No. 1, 2010, 9-16.

Zhai, et al., "Syntheses of PVA/Starch Grafted Hydrogels by Irradiation", Carbohydrate Polymers, 50, 2002, 295-303.

Bentec Medical Product Brochure dated Nov. 20, 2011; http://web.archive.org/web/20111120002601/http://www.bentecmed.com/new-products.

Bentec Medical Product Brochure dated Nov. 20, 2012; http://web.archive.org/web/20121120080102/http://www.bentecmed.com/medical-device.

* cited by examiner

ABSORBENT CLEANING AND SECUREMENT DEVICES AND METHODS

RELATED APPLICATIONS

This application claims priority to U.S. Provisional Application No. 61/862,172 filed on Aug. 5, 2013 and titled, "Absorbent Cleaning and Securement Device," which is hereby incorporated by reference in its entirety.

TECHNICAL FIELD

The present disclosure relates generally to absorbent cleaning devices for use during surgical procedures. More particularly, the present disclosure relates to absorbent cleaning devices or similar devices that may be configured to clean gloves, medical appliances, and elongate medical devices. The disclosed absorbent cleaning devices may also be configured to secure medical appliances or elongate medical devices during surgical procedures.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
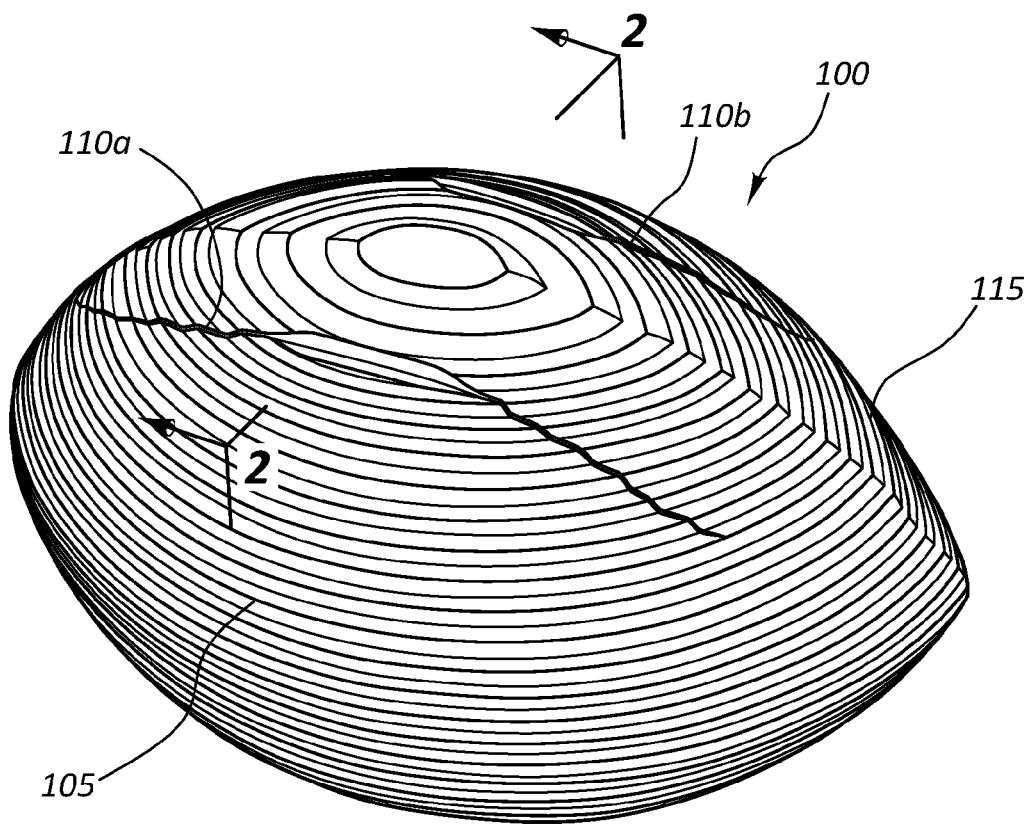
FIG. 1 is a perspective view of an embodiment of an absorbent cleaning device.

An absorbent cleaning device may be used during a surgical procedure to clean gloves, medical appliances, and elongate medical devices. Some such surgical procedures may include, but are not limited to, vascular procedures and wire-based interventions. Such surgical procedures may be conducted in ambulatory care centers, catheterization laboratories, electrophysiology departments, hospitals, interventional suites, operating rooms, surgical centers, or other locations. During a surgical procedure, gloves, medical appliances, and elongate medical devices may become soiled by contact with bodily fluids (i.e., blood), tissue fragments, medical contrast media, and/or other matter.

An absorbent cleaning device may be configured to at least partially clean or remove such matter from gloves, medical appliances, and elongate medical devices. For example, during a catheterization a catheter may become at least partially coated with blood and/or other matter. An absorbent cleaning device may comprise an opening configured to accommodate and come into contact with a portion of the catheter such that upon agitation or movement of the catheter against the absorbent cleaning device the blood and/or other matter may be at least partially cleaned or removed from the catheter. In some embodiments, the opening may comprise a slit configured to accommodate a portion of a medical appliance or an elongate medical device. In other embodiments, the opening may comprise an elongate channel configured to accommodate a portion of a medical appliance or an elongate medical device. Furthermore, some absorbent cleaning devices may comprise a cleaning solution, a saline solution, and/or an anticoagulant (i.e., heparin). Still further, the absorbent cleaning device may comprise a substantially non-fibrous or non-particulate polymer. In certain embodiments, the polymers may or may not be cross-linked. In some examples, the absorbent cleaning device may comprise polyvinyl acetate, polyvinyl alcohol, or polyvinyl fluoride (PVF). In other examples, the absorbent cleaning device may comprise a hydrophilic cross-linked polymer including, but not limited to, polyhydroxyethylmethacrylate (pHEMA), a polyacrylate, a cross-linked polyacrylic acid, and a cross-linked polyamine derivative.

A body, such as the absorbent body of an absorbent cleaning device, may further be configured to secure or otherwise retain a portion of an elongate medical device or instrument during a therapy. For example, during a vascular intervention a practitioner may secure the relative position of a device such as a guide wire by disposing a portion of the guide wire in a slit disposed in the body. Interaction between the guide wire and opposing walls of the slit may then maintain the relative position of the guide wire with respect to the body. Thus, the body may be used to temporarily secure elongate instruments during therapy.

It will be readily understood by one of skill in the art having the benefit of this disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

Figure 2:
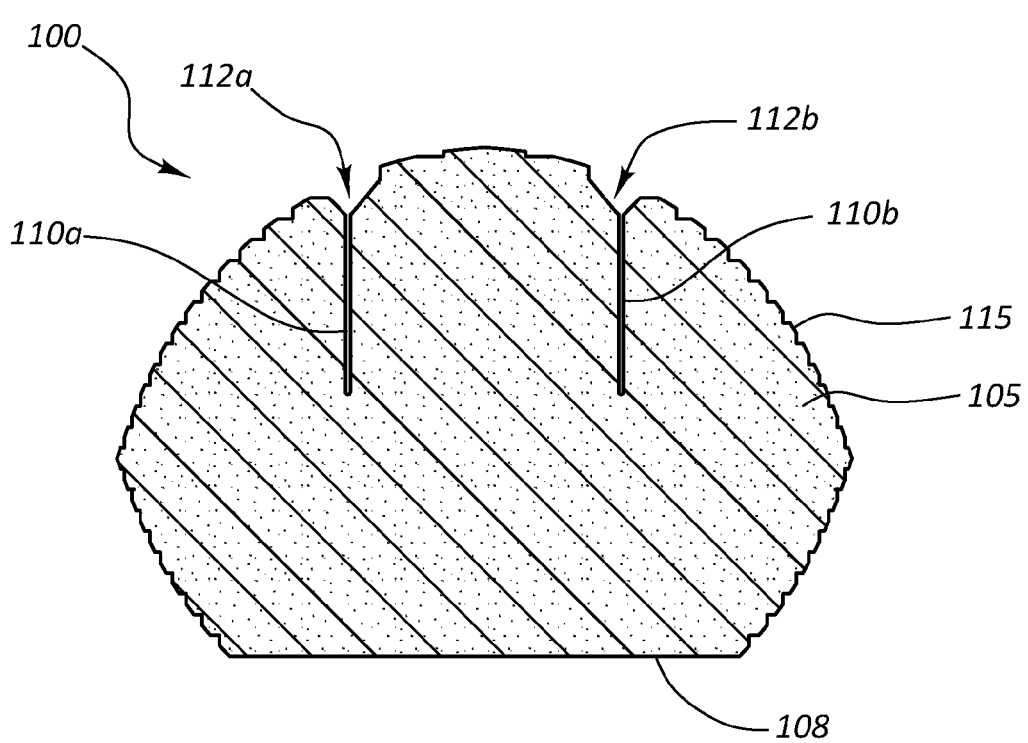
FIG. 2 is a cross-section of the embodiment of FIG. 1 taken through line 2-2.

FIG. 1 is a perspective view of one embodiment of an absorbent cleaning device 100. The illustrated absorbent cleaning device 100 is substantially ovoid, prolate spheroid, or American-football shaped. It will be appreciated by one skilled in the art having the benefit of this disclosure that absorbent cleaning devices as described herein may comprise other shapes including, but not limited to, cones, cubes, cuboids, cylinders, dodecahedrons, octahedrons, prisms, pyramids, spheres, hemispheres, tetrahedrons, and modifications thereof. The absorbent cleaning device 100 illustrated in FIG. 1 comprises a body 105 and two openings 110a, 110b disposed in the body 105. In the illustrated embodiment, the openings 110a, 110b comprise slits. FIG. 2 is a cross-section of the absorbent cleaning device 100 of FIG. 1 taken through line 2-2. As illustrated, the absorbent cleaning device further comprises substantially V-shaped notches 112a, 112b at or adjacent an outside surface 115 of the body 105 and the openings or slits 110a, 110b. In other embodiments, the notches 112a, 112b may be substantially U-shaped or otherwise shaped. The notches 112a, 112b may facilitate introduction of a medical appliance or an elongate medical device into the openings or slits 110a, 110b without additional manipulation of the openings or slits 110a, 110b. For example, the notch or notches 112a, 112b may be configured to guide a medical appliance or elongate medical device into the slit or slits 110a, 110b. Slits 110a, 110b within the scope of this disclosure may also lack notches 112a, 112b. For example, narrow portions of the slits 110a, 110b may extend to or adjacent to the outside surface 115 of the body 105. Devices within the scope of this disclosure may comprise more or fewer than two openings. For example, a body, such as body 105, may comprise one, two, three, four, five, or more openings. Also, other configurations of the openings 110a, 110b including, but not limited to, apertures, cavities, channels, holes, indentations, tunnels, and modifications thereof, are within the scope of this disclosure.

In some embodiments, the body 105 may comprise an absorbent material. In other embodiments, the body 105 may further comprise a coating or covering. In yet other embodiments, the absorbent material and/or coating may be at least partially impregnated with an anticoagulant. For example, the absorbent material may be at least partially impregnated with heparin. The anticoagulant may be used to control, limit, and/or prevent coagulation of bodily fluids on the surface 115 of the absorbent cleaning device 100, as coagulated blood on the surface 115 of the absorbent cleaning device 100 may inhibit and/or interfere with the cleaning capabilities or properties of the absorbent cleaning device 100. The anticoagulant may also control, limit, and/or reduce thrombogenesis on the surface of the absorbent cleaning device 100.

In some embodiments, the absorbent material may comprise a polymer. In certain embodiments, the polymer may comprise polyvinyl acetate, polyvinyl alcohol, or polyvinyl fluoride (PVF). In certain embodiments, the polymers may or may not be cross-linked. In certain other embodiments, the polymer may comprise a hydrophilic cross-linked polymer including, but not limited to, polyhydroxyethylmethacrylate (pHEMA), a polyacrylate, a cross-linked polyacrylic acid, and a cross-linked polyamine derivative. In yet other embodiments, the absorbent cleaning device 100 may comprise a hypoallergenic material. In still other embodiments, the absorbent material may be substantially non-fibrous or non-particulate. The absorbent cleaning device 100 may also comprise a substantially non-fibrous or non-particulate absorbent material, as fibers or particles, which, if introduced or released into an individual or a patient, may generate granulomas or be otherwise deleterious.

The absorbent material may comprise pores such that the body 105 may be configured to absorb two or more times its dry weight in fluid. In other embodiments, the body 105 may be configured to absorb 12 or more times its dry weight in fluid, including four times or more and eight times or more its dry weight in fluid. Additionally, the absorbent cleaning device 100 may be at least partially impregnated with a cleaning solution. In some embodiments, the absorbent cleaning device 100 may be at least partially impregnated with a saline solution. The absorbent cleaning device 100 may also be configured to be coupled to a fluid reservoir (i.e., an IV bag). The fluid reservoir may contain an anticoagulant, cleaning solution, and/or saline solution and be configured to keep the absorbent cleaning device 100 hydrated or moist. In some embodiments, the absorbent cleaning device 100 may be configured to hydrate or moisten a portion of an accommodated medical appliance or elongate medical device, or the absorbent cleaning device 100 may be configured to maintain an accommodated medical appliance or elongate medical device in a hydrated or moistened state. For example, a guide wire or other device may be configured with a hydrophilic coating. Maintenance of the hydration of such a coating may increase the lubricity, cleanliness, and/or handling of the guide wire during surgery or therapy.

In some embodiments, the body 105 may be compressible when pressure is applied to the body 105, and the body 105 may substantially return to an uncompressed configuration when pressure is released. Stated another way, the body 105 may comprise a shape-memory material such that the body 105 may at least generally or substantially return to an uncompressed state upon removal of an applied force and/or pressure.

The body 105, as illustrated in FIG. 2, may comprise a substantially planar surface 108 and the substantially planar surface 108 may be substantially oval. In other embodiments, wherein the body 105 is not substantially ovoid, the substantially planar surface 108 may comprise another shape including, but not limited to, a circle, octagon, parallelogram, pentagon, rectangle, square, trapezoid, triangle, or modification thereof. The substantially planar surface 108 may control and/or reduce movement or rolling of the absorbent cleaning device 100 when it is placed or set on a surface, such as a patient's body. Thus, the shape of the body 105 generally, including the presence or position of a substantially planar surface 108 may tend to stabilize the body 105 during use. In some other embodiments, the absorbent cleaning device 100 may comprise a first substantially planar surface on a first surface of the body 105 and a second substantially planar surface on a second surface of the body 105. Such a configuration may allow or permit two or more absorbent cleaning devices 100 to be stacked on top of one another.

In some embodiments, the absorbent cleaning device 100 may further comprise a mechanism configured to adhere or secure the absorbent cleaning device 100 to a surface (i.e., a table or wall). In one embodiment, an adhesive may be coupled to or present on at least a portion of the body 105, for example, on a portion of the substantially planar surface 108. The adhesive may also be coupled to or present on at least a portion of the surface 115 of the absorbent cleaning device 100 not comprising a substantially planar surface 108. In some embodiments, an adhesive may be covered prior to use. In one example, a practitioner may peel off or remove a covering to expose an adhesive on at least a portion of the surface 115 of the absorbent cleaning device 100. The practitioner may then adhere or secure the absorbent cleaning device 100 to a surface during a medical procedure or therapy. A practitioner may also opt not to expose the adhesive, allowing the practitioner to lift or otherwise displace the absorbent cleaning device 100 during therapy.

Referring to FIGS. 1 and 2, in the illustrated embodiment, the openings 110a, 110b comprise slits extending inwardly from the outside surface 115 of the body 105. In some embodiments, the openings or slits 110a, 110b may extend from the substantially planar surface 108 of the body 105. In the illustrated embodiment, the openings or slits 110a, 110b extend from a surface other than the substantially planar surface 108. In another embodiment, a depth of the slits 110a, 110b may extend less than one-half of a depth of the body 105 along the direction of the slit 110a, 110b. In other embodiments, the absorbent cleaning device 100 may not comprise a substantially planar surface 108. Further, the openings or slits 110a, 110b may also be positioned at any location on the body 105. There may be more than one opening, and/or the opening or openings may extend in a direction perpendicular to the configuration illustrated in FIG. 1.

Further, the openings or slits 110a, 110b may extend in a direction perpendicular to a substantially planar surface 108 of the body 105 or at any other angle with respect to a substantially planar surface 108 of the body 105. The openings or slits 110a, 110b may extend from an outside surface of the body 105 along a radius of a circular or substantially circular cross-section of the body 105 and/or extend toward a centroid or focus of a cross-section of the body 105. Additionally or alternatively, the openings or slits 110a, 110b may extend along a maximum direction of a cross-section of the body 105, meaning the direction is a maximum dimension across the cross-section. The openings or slits 110a, 110b may be configured to extend into the body 105 while allowing the body 105 sufficient structure to generally maintain its shape. Other configurations of the opening or openings are also contemplated.

The openings or slits 110a, 110b of FIGS. 1 and 2 are configured to accommodate a portion of a medical appliance or an elongate medical device. In some embodiments, the elongate medical device may be selected from at least one of a catheter, introducer, snare, tube, and/or wire. Other elongate medical devices are also within the scope of this disclosure. In some embodiments, the opening or slits 110a, 110b may be configured to clean the medical appliance or the elongate medical device. In other embodiments, the opening or slits 110a, 110b may be configured to retain, hold, or otherwise secure the elongate medical device. For example, the slits 110a, 110b may hold or secure the position of one or more guide wires during a wire-based intervention. For example, a practitioner may dispose a portion of a guide wire within a slit 110a or 110b during a procedure. Interaction between opposing walls of the slit 110a or 110b and the guide wire may tend to maintain the position of the guide wire with respect to the body 105. The practitioner may subsequently remove the guide wire from the slit 110a or 110b and/or displace the entire body 105 to displace the guide wire.

The slits 110a, 110b may comprise narrow cuts in the body 105. The shape and form of the body 105, along with the narrowness of the slits 110a, 110b may tend to maintain the slits 110a, 110b in a closed configuration. In other words, opposing walls defined by the slits 110a, 110b may tend to remain in contact with each other when the body 105 is unconstrained. In some embodiments, the slits 110a, 110b may be configured to remain in a closed configuration such that opposing walls of the slits 110a, 110b are in contact when the body 105 is in an unconstrained configuration.

In some embodiments, the body 105 may be cupped or at least partially hollow. In some instances, cupping of the body 105 may tend to introduce a biasing effect to further maintain the closed configuration of the slits 110a, 110b. For example, a lower surface of the body 105 may be cupped and slit or slits 110a, 110b may be disposed on an upper surface of the body 105. The cupped configuration may tend to introduce a stress that will maintain the slits 110a, 110b in a closed configuration. Again, the slits 110a, 110b may be self-closing regardless of whether the body 105 is cupped. Thus, in some embodiments, an external force or pressure may not be required to transition the slits 110a, 110b from an open configuration to a closed configuration.

Referring again to FIGS. 1 and 2, the illustrated body 105 comprises a textured outside surface 115. As illustrated, the outside surface 115 comprises a series of annular steps extending circumferentially around the body 105. Other patterns or textures are also within the scope of this disclosure. For example, the surface of the body 105 may be substantially covered with a series of dimples. The textured surface 115 may act to enhance friction upon contact and/or agitation between gloves, medical appliances, or elongate medical devices and the textured surface 115 of the absorbent cleaning device 100. Such friction may enhance the ability of the absorbent cleaning device 100 to remove bodily fluids, tissue fragments, medical contrast media, and/or other matter from the surface of gloves, medical appliances, or elongate medical devices. In other embodiments, the surface 115 may be substantially smooth.

Figure 3A:
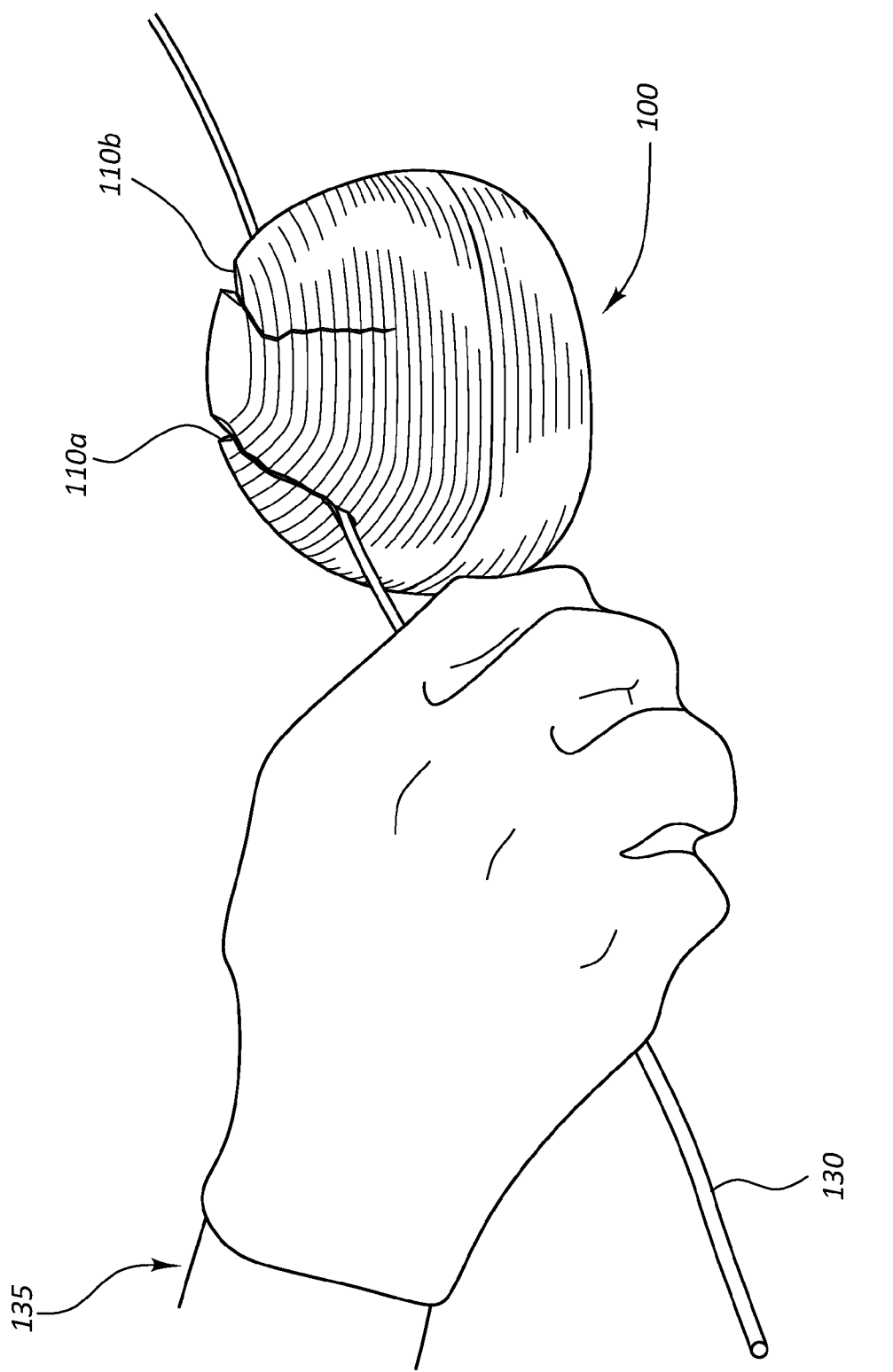
FIG. 3A depicts a method of using the absorbent cleaning device of FIG. 1 to clean or secure a portion of an elongate medical device.

FIG. 3A illustrates an exemplary method for using an absorbent cleaning device 100 as disclosed herein. In the exemplary method, a user 135 may introduce a portion of an elongate medical device 130 into one of the slits 110a, 110b of the absorbent cleaning device 100. In some embodiments, the illustrated absorbent cleaning device 100 may be used to clean other types of medical appliances. The user 135 may then agitate or rub the portion of the elongate medical device 130 against walls of the slit 110a or 110b to clean and/or remove matter from the surface of the elongate medical device 130. The user 135 may also transition the elongate medical device 130 between at least a first position and a second position within the slit 110a or 110b such that the surface of the elongate medical device 130 is at least partially cleaned. In another embodiment of the method of FIG. 3A, the method may comprise the step of at least partially impregnating or re-impregnating the absorbent cleaning device 100 with a cleaning solution and/or a saline solution.

Figure 3B:
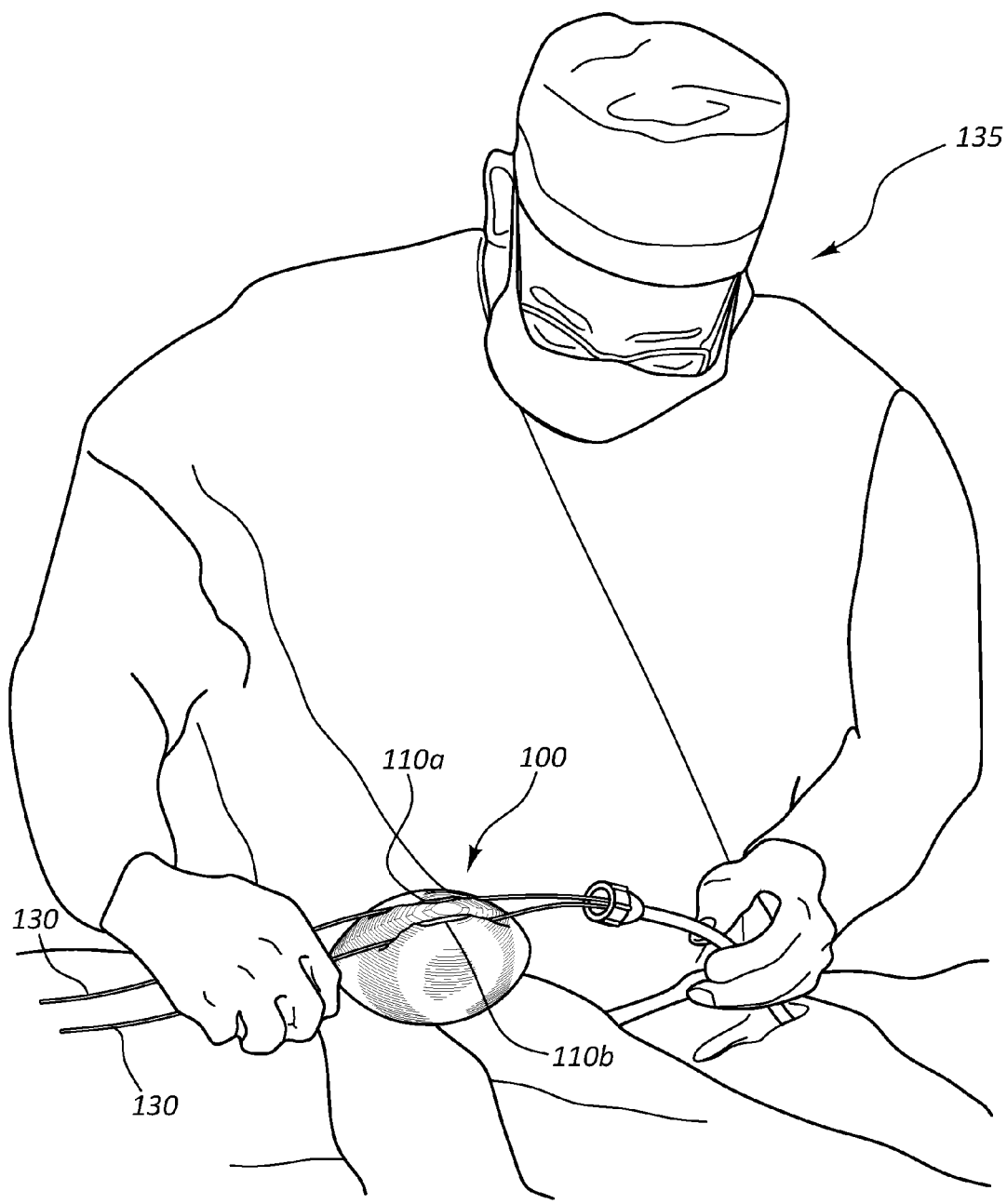
FIG. 3B depicts a method of using the absorbent cleaning device of FIG. 1 to secure elongate medical devices.

FIG. 3B illustrates an exemplary method of using the absorbent cleaning device 100 of FIG. 1 to secure two elongate medical devices 130. In the exemplary method, the user 135 may introduce portions of elongate medical devices 130 into slits 110a, 110b of an absorbent cleaning device 100. The user 135 may then adjust positions of the portions of the elongate medical devices 130 within the slits 110a, 110b such that the elongate medical devices 130 are secured with respect to the body 105. In some embodiments, opposing walls of the slits 110a, 110b may tend to contact the elongate medical devices 130 when the absorbent cleaning device 130 is unconstrained.

As illustrated in FIG. 3B, the slits 110a, 110b may be configured to retain or secure elongate medical devices 130 disposed therein. Such retention or securement may result from friction between the opposing walls of the slits 110a, 110b and the elongate medical device 130. For example, the slits 110a, 110b may be configured to retain an elongate medical device 130 disposed therein through friction between opposing walls of the slits 110a, 110b and the elongate medical device 130. In some embodiments, opposing walls of the slits 110a, 110b may tend to contact the elongate medical device 130 when the absorbent cleaning device 100 is unconstrained. The user 135 may introduce one or more elongate medical devices 130 into one or more slits 110a, 110b such that the elongate medical device or devices 130 are retained or secured in place. For example, a catheter may be held or secured with respect to the body by introduction of the catheter into a slit of an absorbent cleaning device during a surgical procedure. In some embodiments, the absorbent cleaning device 100 may comprise more or fewer than two slits 110a, 110b. For example, a body, such as body 105, may comprise one, two, three, four, five, or more slits. Consequently, in other embodiments, the absorbent cleaning device 100 may be configured to retain or secure more or fewer than two elongate medical devices 130. A body 105 configured to secure other devices or components may or may not be configured as a cleaning absorbent device.

Figure 4:
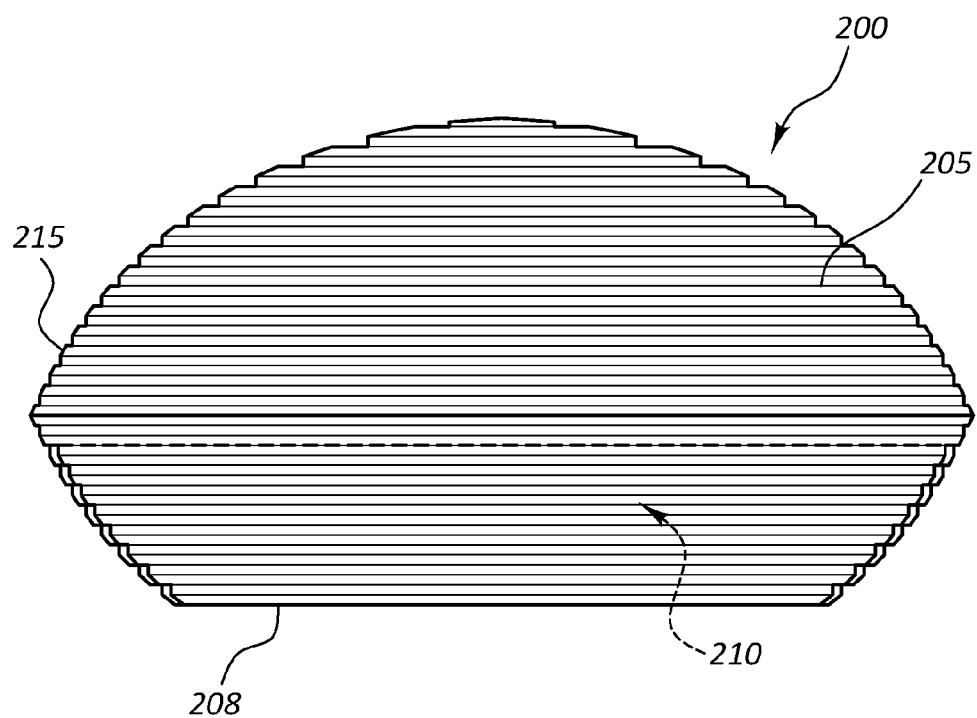
FIG. 4 is a side view of another embodiment of an absorbent cleaning device, wherein the position of one configuration of an opening is indicated by a dashed line.
Figure 5:
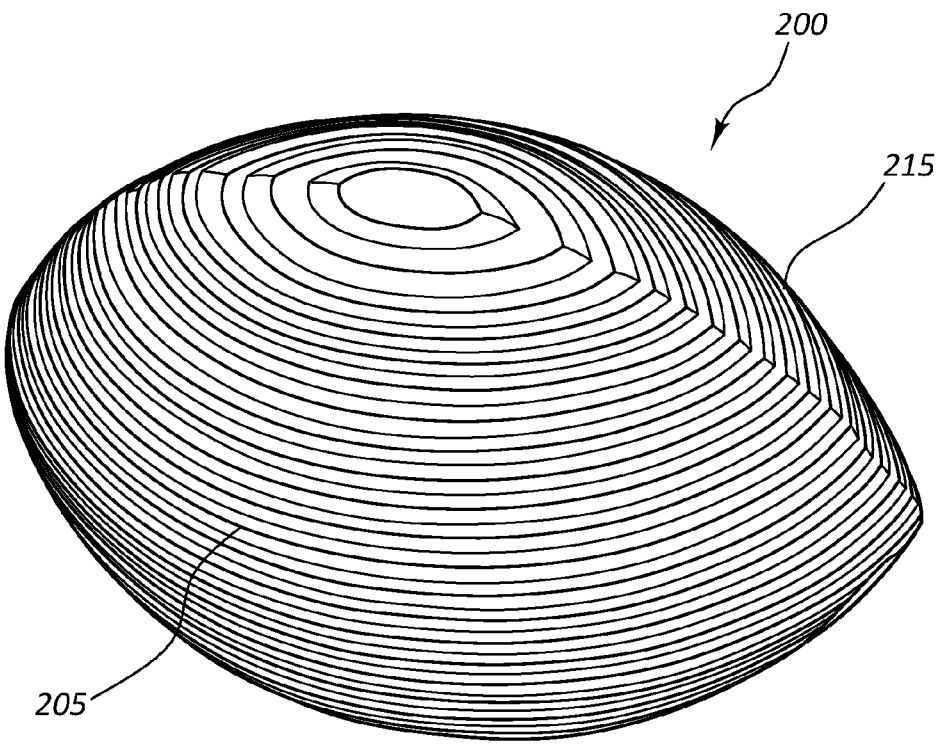
FIG. 5 is a perspective view of the top of the absorbent cleaning device of FIG. 4.
Figure 6:
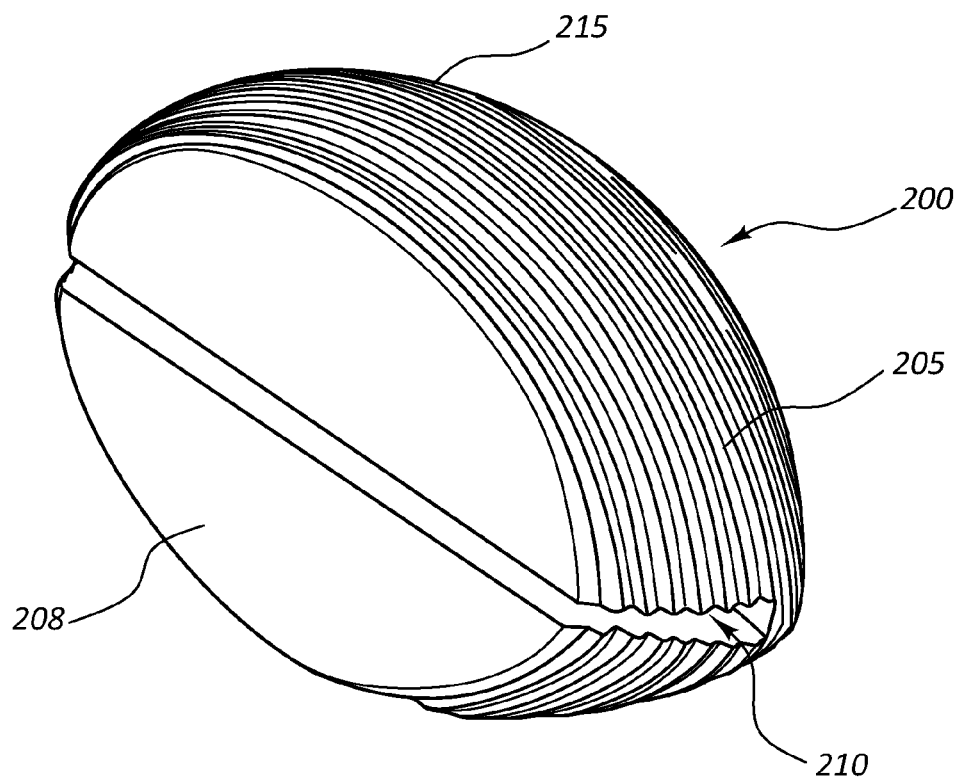
FIG. 6 is a perspective view of the bottom of the absorbent cleaning device of FIG. 4.

FIG. 4 is a side view of one embodiment of an absorbent cleaning device 200. FIG. 5 is a perspective view of the top of the absorbent cleaning device 200 of FIG. 4, and FIG. 6 is a perspective view of the bottom of the absorbent cleaning device 200 of FIG. 4. The illustrated absorbent cleaning device 200 is substantially ovoid, prolate spheroid, or American-football shaped. As discussed above, it will be appreciated by one skilled in the art having the benefit of this disclosure that absorbent cleaning devices as described herein may comprise other shapes including, but not limited to, cones, cubes, cuboids, cylinders, dodecahedrons, octahedrons, prisms, pyramids, spheres, hemispheres, tetrahedrons, and modifications thereof. The dashed line of FIG. 4 indicates the position of an opening 210 in one configuration. As illustrated in FIGS. 4 and 6, the opening 210 comprises an elongate channel. Other configurations of the opening 210, however, including, but not limited to, apertures, cavities, holes, indentations, slits, tunnels, and modifications thereof, are also within the scope of this disclosure.

The embodiment of FIGS. 4-7 may include components that resemble components of the embodiment of FIGS. 1 and 2 in some respects. For example, the embodiment of FIG. 4 includes a body 205 that may resemble the body 105 of FIG. 1. It will be appreciated that all the illustrated embodiments have analogous features. Accordingly, like features are designed with like reference numerals, with leading digits added to increment each reference numeral by 100. (For instance, the body is designated "105" in FIG. 1 and an analogous body is designated as "205" in FIG. 4.) Relevant disclosure set forth above regarding similarly identified features thus may not be repeated hereafter. Moreover, specific features of the absorbent cleaning device and related components shown in FIG. 4 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the absorbent cleaning device and related components of FIG. 4. Any suitable combination of the features, and variations of the same, described with respect to the absorbent cleaning device and components illustrated in FIG. 1, can be employed with the absorbent cleaning device and components of FIG. 4, and vice versa. This pattern of disclosure applies equally to further embodiments depicted in subsequent figures and/or described hereafter.

Referring to FIGS. 4-6, the absorbent cleaning device 200 comprises a body 205 and an opening 210 disposed in the body 205. Disclosure above regarding the position, orientation, geometry, or other characteristics of the openings or slits 110a, 110b of FIGS. 1-3 may analogously be applied to the opening 210 of FIGS. 4-6 and vice versa. In some embodiments, the body 205 may comprise an absorbent material. In other embodiments, the body 205 may further comprise a coating or covering. In yet other embodiments, the absorbent material and/or coating may be at least partially impregnated with an anticoagulant. For example, the absorbent material may be at least partially impregnated with heparin. The anticoagulant may be used to control, limit, and/or prevent coagulation of bodily fluids on a surface 215 of the absorbent cleaning device 200, as coagulated blood on the surface 215 of the absorbent cleaning device 200 may inhibit and/or interfere with the cleaning capabilities or properties of the absorbent cleaning device 200. The anticoagulant may also control, limit, and/or reduce thrombogenesis on the surface 215 of the absorbent cleaning device 200. Embodiments of absorbent cleaning devices comprising both slits (such as 110a, 110b of FIGS. 1-3) and one or more additional openings, for example channels) (such as 210 of FIGS. 4-6) are within the scope of this disclosure.

As discussed above, the absorbent material may comprise a polymer. In some embodiments, the polymer may comprise polyvinyl acetate or polyvinyl alcohol. In another embodiment, the polymer may comprise polyvinyl fluoride (PVF). In certain embodiments, the polymers may or may not be cross-linked. In other embodiments, the polymer may comprise a hydrophilic cross-linked polymer including, but not limited to, polyhydroxyethylmethacrylate (pHEMA), a polyacrylate, a cross-linked polyacrylic acid, and a cross-linked polyamine derivative. In yet other embodiments, the absorbent cleaning device 200 may comprise a hypoallergenic material. In still other embodiments, the absorbent material may be substantially non-fibrous or non-particulate, as fibers or particles, which, if introduced or released into an individual or a patient, may generate granulomas or be otherwise deleterious.

The absorbent material may comprise pores such that the body 205 may be configured to absorb two or more times its dry weight in fluid. In other embodiments, the body 205 may be configured to absorb 12 or more times its dry weight in fluid, including four times or more and eight times or more its dry weight in fluid. Additionally, the absorbent cleaning device 200 may be at least partially impregnated with a cleaning solution. In some embodiments, the absorbent cleaning device 200 may be at least partially impregnated with a saline solution. The absorbent cleaning device 200 may also be configured to be coupled to a fluid reservoir (i.e., an IV bag). The fluid reservoir may contain an anticoagulant, cleaning solution, and/or saline solution and be configured to keep the absorbent cleaning device 200 hydrated or moist.

In an embodiment, the body 205 may be compressible when pressure is applied to the body 205, and the body 205 may substantially return to an uncompressed configuration when pressure is released. Stated another way, the body 205 may comprise a shape-memory material such that the body 205 may at least generally or substantially return to an uncompressed state upon removal of an applied force and/or pressure.

The body 205 of FIG. 4 comprises a substantially planar surface 208 wherein the substantially planar surface 208 is substantially oval (see FIG. 6). In other embodiments, wherein the body 205 is not substantially ovoid, the substantially planar surface 208 may comprise another shape including, but not limited to, a circle, octagon, parallelogram, pentagon, rectangle, square, trapezoid, triangle, or modification thereof. The substantially planar surface 208 may control and/or reduce movement or rolling of the absorbent cleaning device 200 when it is placed or set on a surface, such as a patient's body. Thus, the shape of the body 205 generally, including the presence or position of a substantially planar surface 208 may tend to stabilize the body 205 during use.

In some embodiments, the absorbent cleaning device 200 may further comprise a mechanism configured to adhere or secure the absorbent cleaning device 200 to a surface (i.e., a table or a wall). In one embodiment, an adhesive may be coupled to or present on at least a portion of the body 205, for example, on a portion of the substantially planar surface 208. The adhesive may also be coupled to or present on at least a portion of the surface 215 of the absorbent cleaning device 200 not comprising a substantially planar surface 208. In some embodiments, an adhesive may be covered prior to use. In one example, a practitioner may peel off or remove a covering to reveal an adhesive on at least a portion of the surface 215 of the absorbent cleaning device 200. The practitioner may then adhere or secure the absorbent cleaning device 200 to a surface during a medical procedure or therapy. A practitioner may also opt not to expose the adhesive, allowing the practitioner to lift or otherwise displace the absorbent cleaning device 200 during therapy.

Referring to FIGS. 4 and 6, in the illustrated embodiment, the opening 210 comprises a channel extending inwardly from an outside surface 215 of the body 205. In some embodiments, as illustrated, the channel may extend from the substantially planar surface 208 of the body 205. In another embodiment, a depth of the channel may be less than one-half of a depth of the body 205 along the direction of the channel, and a width of the channel may be less than one-fourth of the depth of the channel. In other embodiments, the absorbent cleaning device 200 may not comprise a substantially planar surface 208. The opening may also be positioned at other locations and in other orientations on the body 205. For example, the opening 210 may comprise a tunnel passing through the absorbent cleaning device 200. In other examples, there may be more than one opening 210, or the opening 210 may extend in a direction perpendicular to the configuration illustrated in FIGS. 4 and 6. The opening 210 may extend into the body 205 while retaining sufficient body 105 structure that the body 205 tends to maintain its shape. Other configurations of the opening 210 are also contemplated.

Figure 7:
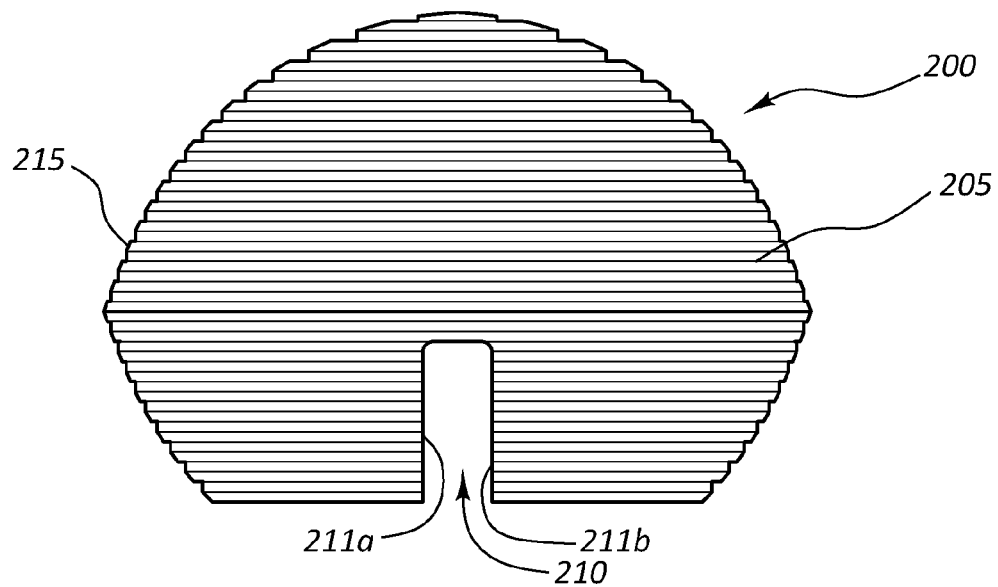
FIG. 7 is an end view of the absorbent cleaning device of FIG. 4.

FIG. 7 is an end view of the embodiment of the absorbent cleaning device 200 of FIG. 4. As illustrated, the opening or channel 210 comprises opposing walls 211a, 211b. The opposing walls 211a, 211b may be displaceable toward each other. For example, a user may apply a force to the body 205 that inwardly biases or displaces the opposing walls 211a, 211b toward one another. Upon displacement of the opposing walls 211a, 211b, the walls 211a, 211b may contact each other and/or a portion of a medical appliance or elongate medical device present in the channel 210. The channel 210 of FIGS. 4, 6, and 7 is configured to accommodate a portion of a medical appliance or an elongate medical device. In some embodiments, the elongate medical device may be selected from at least one of a catheter, introducer, snare, tube, and/or wire. Other elongate medical devices are also within the scope of this disclosure.

Referring to FIGS. 4-7, the illustrated body 205 comprises a textured outside surface 215. As illustrated, the outside surface 215 comprises a series of annular steps extending circumferentially around the body 205. Other patterns or textures are also within the scope of this disclosure. For example, the surface of the body 205 may be substantially covered with a series of dimples. The textured surface 215 may act to enhance friction upon contact and/or agitation between gloves, medical appliances, or elongate medical devices and the textured surface 215 of the absorbent cleaning device 200. Such friction may enhance the ability of the absorbent cleaning device 200 to remove bodily fluids, tissue fragments, medical contrast media, and/or other matter from the surface of gloves, medical appliances, or elongate medical devices. In other embodiments, the surface 215 may be substantially smooth.

Figure 8:
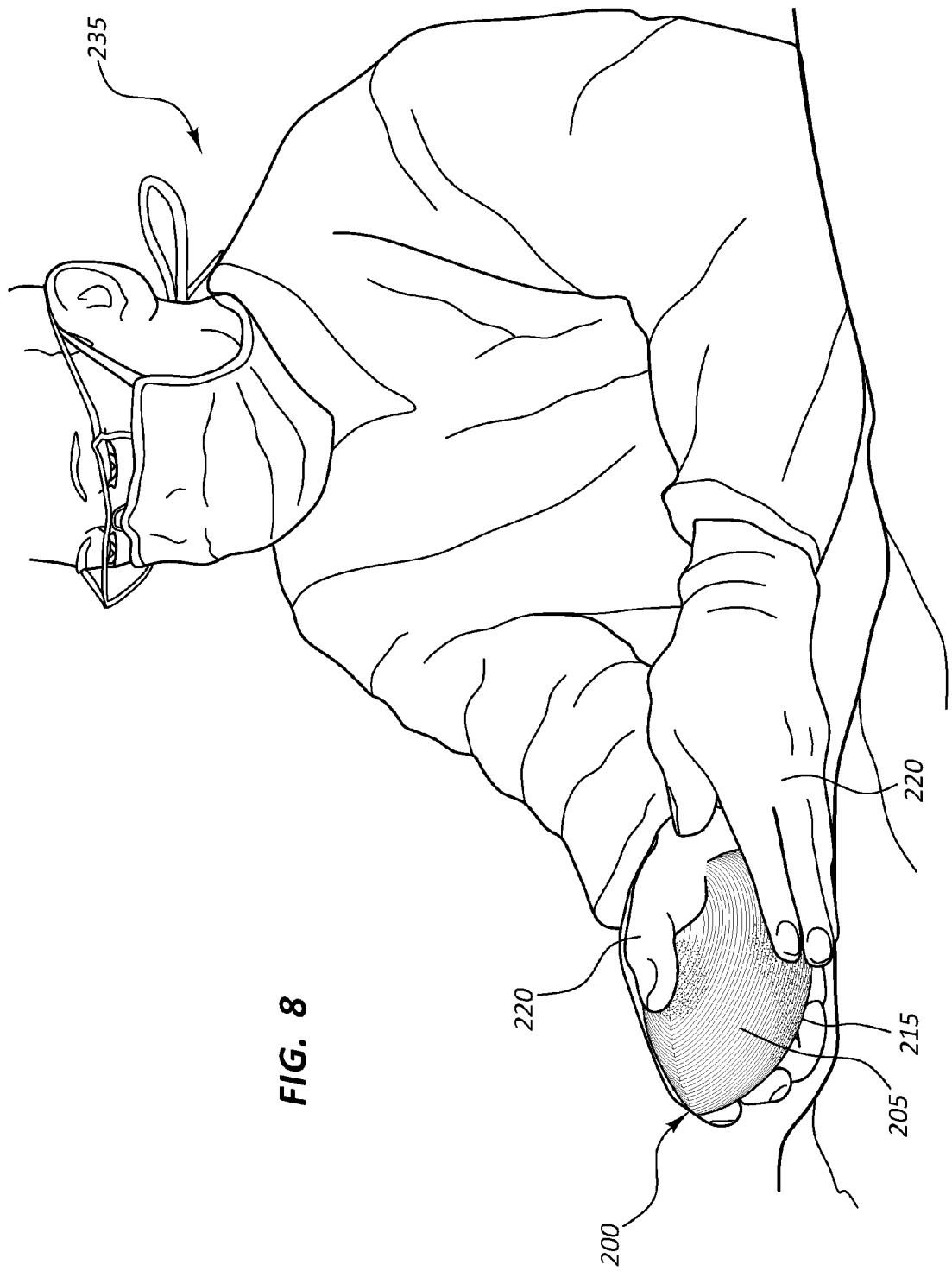
FIG. 8 depicts a method of using the absorbent cleaning device of FIG. 4 to clean a glove.

FIG. 8 illustrates a first exemplary method for using an absorbent cleaning device 200 as disclosed herein. In the method of FIG. 8, a user 235 may contact a soiled glove or gloves 220 with the absorbent cleaning device 200. The user 235, such as a doctor or other medical practitioner, may then agitate or move the soiled gloves 220 over the outside surface 215 of the body 205 such that at least a portion of the bodily fluids, tissue fragments, medical contrast media, and/or other matter disposed on the gloves 220 are removed from the gloves 220 and remain on the absorbent cleaning device 200 such that the outside surface 215 may remain at least partially free of such matter. In some embodiments, the matter may be absorbed or wicked into the absorbent cleaning device 200. In another embodiment of the method of FIG. 8, the method may comprise the step of at least partially impregnating or re-impregnating the absorbent cleaning device 200 with a cleaning solution and/or a saline solution. The user 235 may also use the absorbent cleaning device 200 to maintain hydrated or moist gloves 220 during a surgical procedure.

Figure 9:
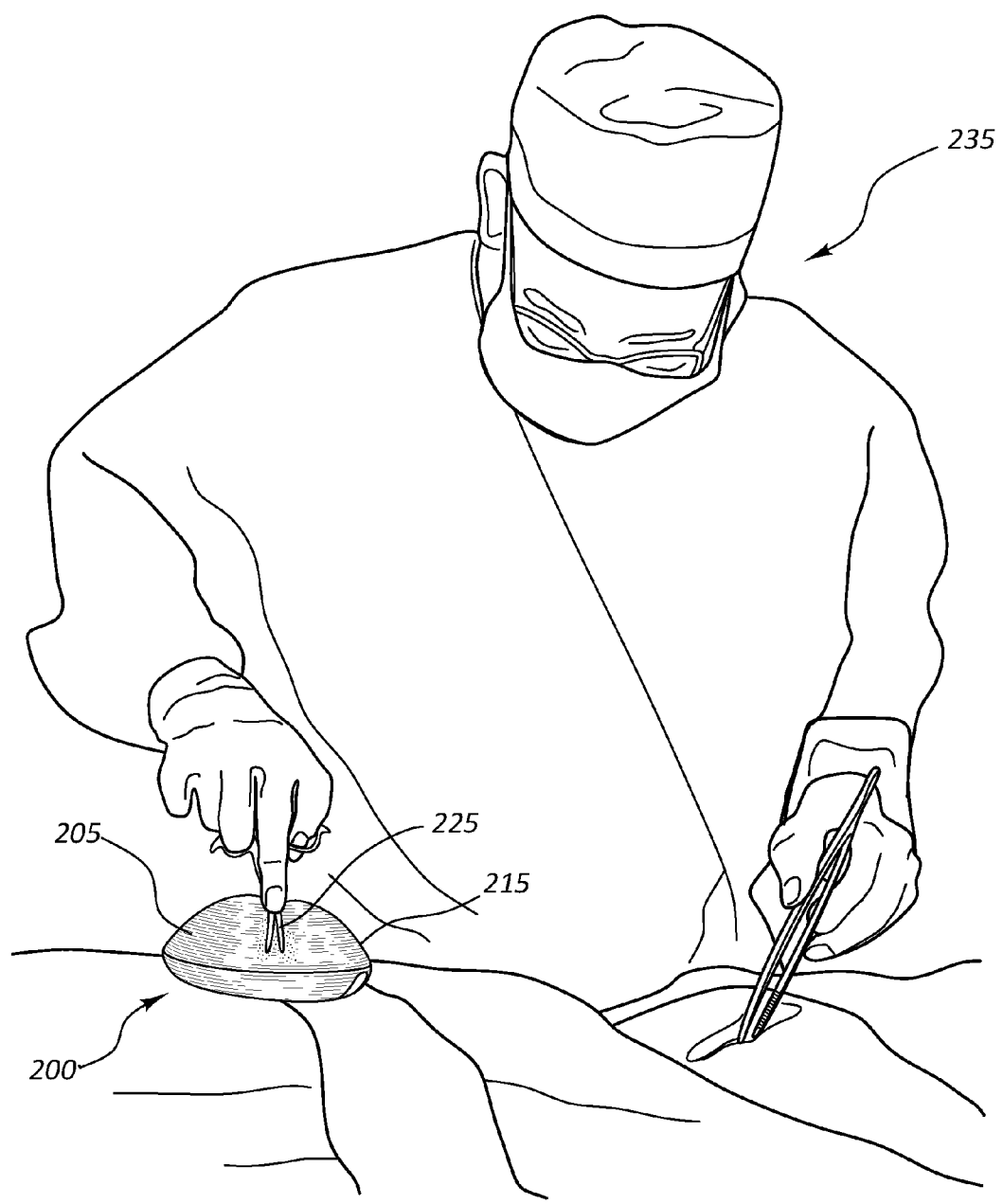
FIG. 9 depicts a method of using the absorbent cleaning device of FIG. 4 to clean a medical appliance.

FIG. 9 illustrates another exemplary method for using an absorbent cleaning device 200 as disclosed herein. In the exemplary method, the user 235 may contact a soiled medical appliance 225 with the absorbent cleaning device 200. The user 235, such as a doctor or other medical practitioner, may agitate or move the soiled medical appliance 225 over the outside surface 215 of the body 205 such that at least a portion of the bodily fluids, tissue fragments, medical contrast media, and/or other matter disposed on the medical appliance 225 are removed from the medical appliance 225 and remain on the absorbent cleaning device 200. In some embodiments, the matter may be absorbed or wicked into the absorbent cleaning device 200. In another embodiment of the method of FIG. 9, the method may comprise the step of at least partially impregnating or re-impregnating the absorbent cleaning device 200 with a cleaning solution and/or a saline solution.

Figure 10:
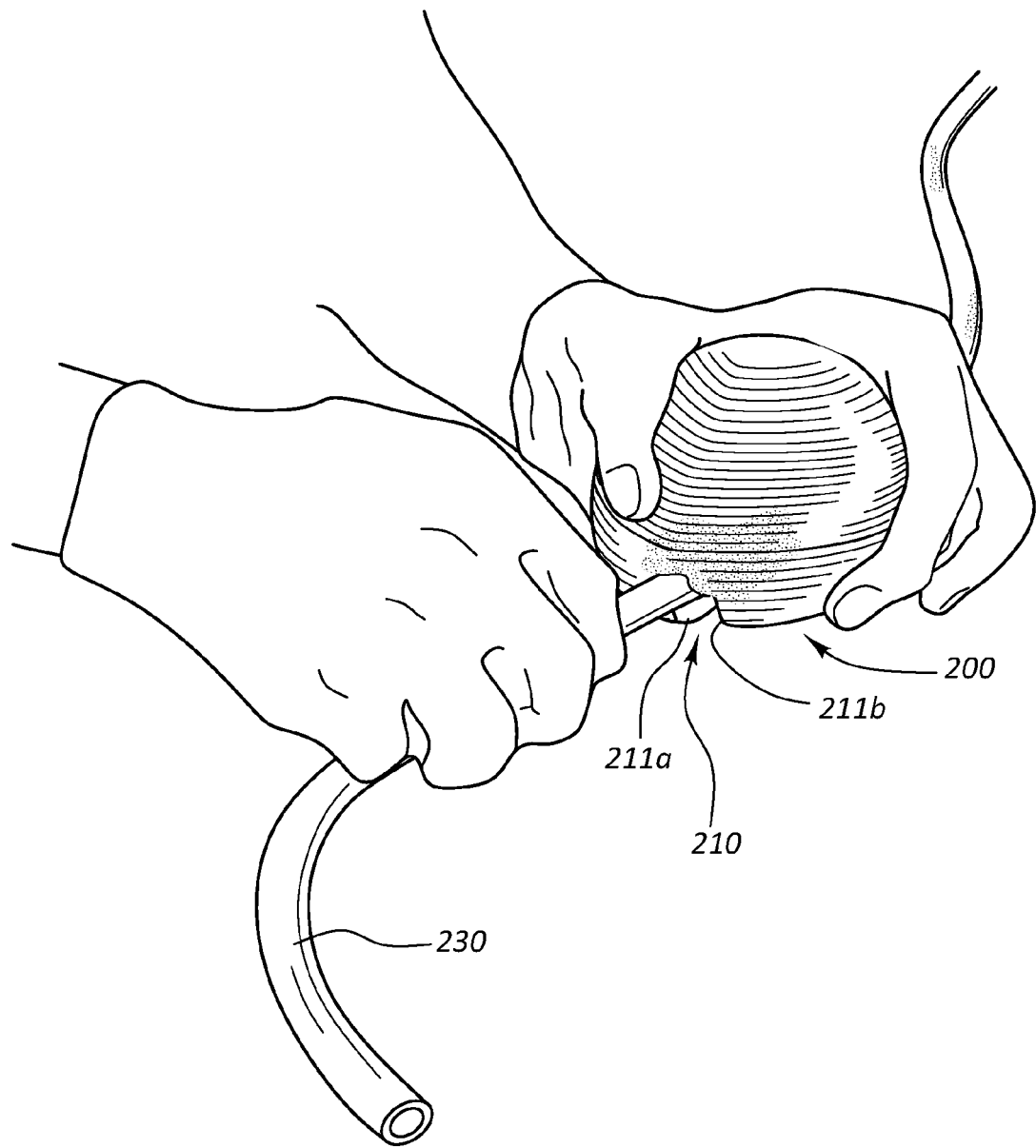
FIG. 10 depicts a method of using the absorbent cleaning device of FIG. 4 to clean a portion of an elongate medical device.

FIG. 10 illustrates yet another exemplary method for using an absorbent cleaning device 200 as disclosed herein. In the exemplary method, the user may introduce a portion of an elongate medical device 230 into the channel 210 of the absorbent cleaning device 200. The user may then compress the channel 210 such that contact is made between the opposing walls 211a, 211b of the channel 210 and a surface of a portion of the elongate medical device 230. The user may then agitate or rub the portion of the elongate medical device 230 against the walls 211a, 211b of the channel 210 to clean and/or remove matter from the surface of the elongate medical device 230. The user may also transition the elongate medical device 230 between at least a first position and a second position within the opening 210 such that the surface of the elongate medical device 230 is at least partially cleaned. In another embodiment of the method of FIG. 10, the method may comprise the step of at least partially impregnating or re-impregnating the absorbent cleaning device 200 with a cleaning solution and/or a saline solution. In some embodiments, the absorbent cleaning device 200 may hydrate or moisten a portion of the elongate medical device 230.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. It is intended that the scope of the invention be defined by the claims appended hereto and their equivalents.

The invention claimed is:

1. An absorbent cleaning device for use during a surgical procedure, the absorbent cleaning device comprising:
 a body comprising:
  an absorbent material;
  a truncated prolate spheroid shape comprising an outer surface; and
  a single component construction; and
 a first opening disposed in the body, the first opening extending from the body outer surface wherein the first opening is normally closed and wherein the first opening is configured to receive an elongate medical device.

2. The absorbent cleaning device of claim 1, wherein the opening comprises a slit.

3. The absorbent cleaning device of claim 2, wherein the slit is configured to retain an elongate medical device disposed therein through friction between the opposing walls of the slit and the elongate medical device.

4. The absorbent cleaning device of claim 2, further comprising a substantially V-shaped notch adjacent the outer surface of the body and the slit, the notch configured to guide an elongate instrument into the slit.

5. The absorbent cleaning device of claim 2, wherein a depth of the slit extends less than one-half of the depth of the body along the direction of the slit.

6. The absorbent cleaning device of claim 2, wherein the body further comprises a substantially planar surface.

7. The absorbent cleaning device of claim 6, wherein the first opening extends from a surface other than the substantially planar surface.

8. The absorbent cleaning device of claim 1, wherein the first opening comprises a channel extending inwardly from the outer surface of the body.

9. The absorbent cleaning device of claim 1, wherein the absorbent cleaning device comprises a second opening disposed in the body.

10. The absorbent cleaning device of claim 9, wherein the second opening comprises a channel extending inwardly from the outer surface of the body.

11. The absorbent cleaning device of claim 10, wherein a depth of the channel extends less than one-half of a depth of the body along the direction of the channel.

12. The absorbent cleaning device of claim 11, wherein a width of the channel is less than one-fourth of the depth of the channel.

13. The absorbent cleaning device of claim 12, wherein the body further comprises a substantially planar surface and the channel extends from the substantially planar surface of the body.

14. The absorbent cleaning device of claim 13, wherein the substantially planar surface is at least partially covered with an adhesive material.

15. The absorbent cleaning device of claim 10, wherein the channel comprises opposing walls, and wherein the opposing walls are displaceable toward each other.

16. The absorbent cleaning device of claim 10, wherein the channel is configured to accommodate a portion of an elongate medical device.

17. The absorbent cleaning device of claim 1, wherein the absorbent material is at least partially impregnated with an anticoagulant.

18. The absorbent cleaning device of claim 1, wherein the absorbent material comprises a polymer and the polymer is selected from at least one of a polyvinyl acetate, polyvinyl alcohol, polyvinyl fluoride (PVF), polyhydroxyethylmethacrylate (pHEMA), polyacrylate, cross-linked polyacrylic acid, or cross-linked polyamine derivative.

* * * * *